United States Patent [19]
Sakai et al.

[11] Patent Number: 5,965,426
[45] Date of Patent: Oct. 12, 1999

[54] PROTEIN DISULFIDE ISOMERASE GENE DERIVED FROM STRAIN OF METHYLOTROPHIC YEAST

[75] Inventors: Yasuyoshi Sakai, Otsu; Nobuo Kato, Kameoka; Yuji Shibano, Toyonaka, all of Japan

[73] Assignee: Suntory Limited, Osaka, Japan

[21] Appl. No.: 08/923,536

[22] Filed: Sep. 4, 1997

[30] Foreign Application Priority Data

Sep. 4, 1996 [JP] Japan ..... 8-234287

[51] Int. Cl.⁶ ............... C12N 9/90; C12N 1/20; C12N 15/00; C07H 21/04
[52] U.S. Cl. ............. 435/233; 435/69.1; 435/252.3; 435/320.1; 435/254.2; 435/254.22; 435/255.4; 536/23.2; 536/23.7; 536/23.74; 530/350; 424/94.5
[58] Field of Search ................ 435/233, 254.2, 435/254.22, 255.4, 320.1, 69.1; 536/23.2, 23.7, 23.74; 530/350

[56] References Cited

U.S. PATENT DOCUMENTS 5,496,719  3/1996  Yamada et al. ............ 435/233

FOREIGN PATENT DOCUMENTS 6-38771    2/1994   Japan .
WO93/25676 12/1993   WIPO .

OTHER PUBLICATIONS

R. Farquhar et al., *Gene*, 108:81–89 (1991).

Y. Sakai et al., *Biochemica et Biophysica Acta*, 1308:81–87 (Jul. 1996).

L.D. Schultz et al., *Annals of the New York Academy of Sciences*, 721:148–157 (1994).

*Primary Examiner*—Ponnathapura Achutamurthy
*Assistant Examiner*—Tekchand Saidha
*Attorney, Agent, or Firm*—Burns, Doane, Swecker & Mathis, L.L.P.

[57] ABSTRACT

A protein derived from a strain of methylotrophic yeast which has a protein disulfide isomerase activity having the amino acid sequence as set forth in SEQ ID No. 1, or protein in which the amino acid sequence has been modified by deletion or addition of one or a few amino acids, or substitution with other amino acid(s) and which has a protein disulfide isomerase activity; and a process for production thereof.

9 Claims, 8 Drawing Sheets

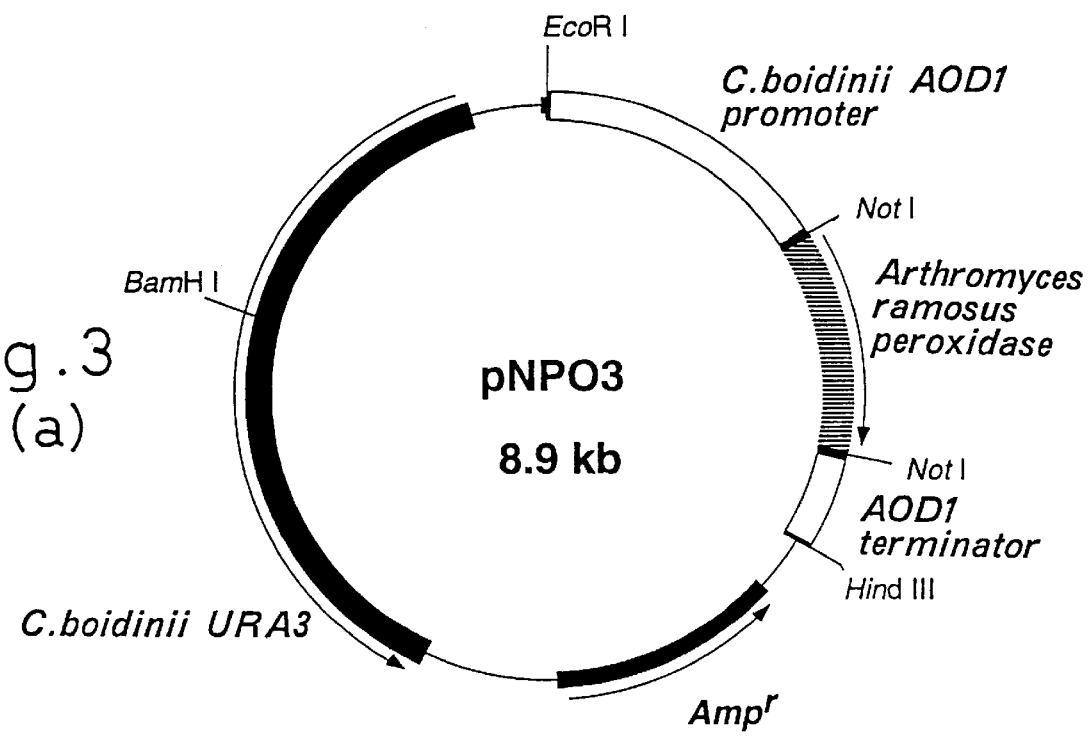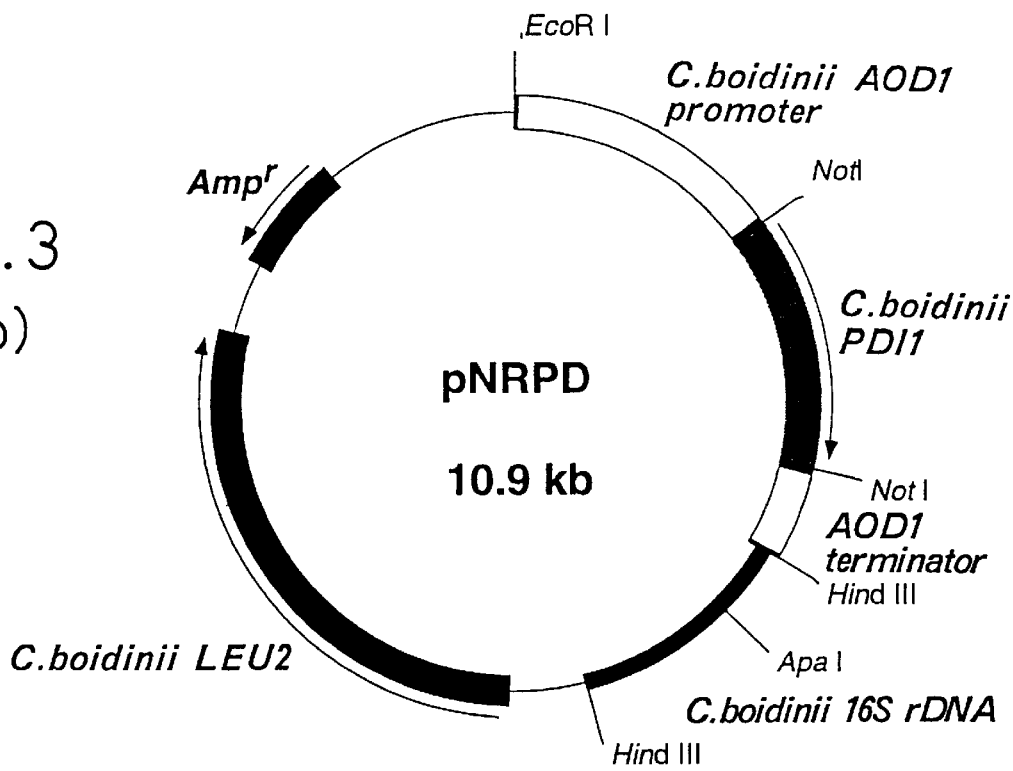

PDI

1: BPP1 strain
2: BP017 strain
3: BUL strain

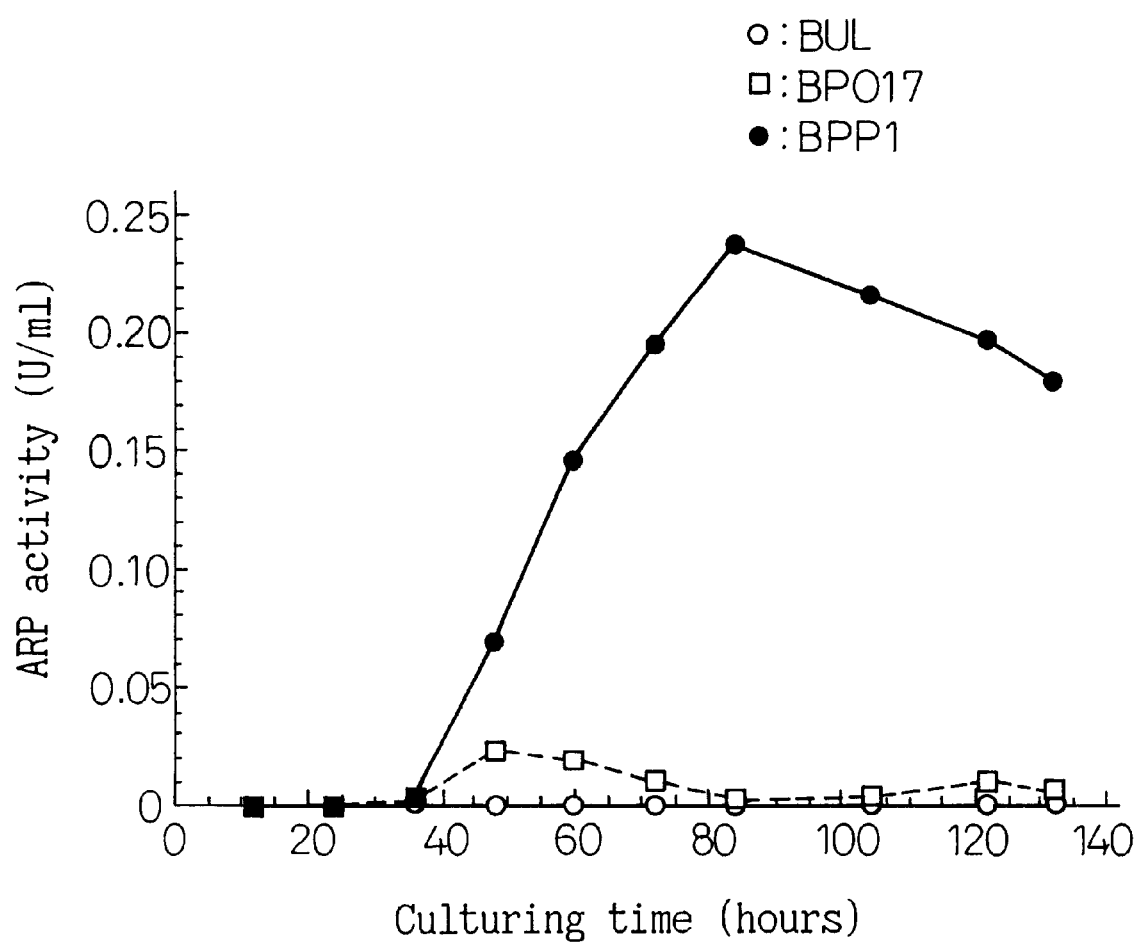

PROTEIN DISULFIDE ISOMERASE GENE DERIVED FROM STRAIN OF METHYLOTROPHIC YEAST

BACKGROUND OF INVENTION

1. Field of Invention

The present invention relates to protein disulfide isomerase, an enzyme which promotes formation of protein conformation by catalyzing formation of disulfide bonds in a protein, and to a gene thereof. The present invention relates, among the protein disulfide isomerases, to protein disulfide isomerase derived from a strain of methylotrophic yeast, a microorganism suitable for industrial production of valuable proteins due to its high efficiency of expression of heterologous genes and secretion of the expression products, and to a gene thereof.

2. Related Art

Protein disulfide isomerase (PDI) is a major protein present in the lumen of the endoplasmic reticulum (referred to hereinafter as ER) and it was first discovered as having an activity which effects oxidative refolding of a reduced RNase (Goldberger, R. F. et al. (1963) J. Biol. Chem. 238: 628–635). PDI is believed to be an enzyme which catalyzes formation of stable conformation by recombining disulfide bonds of secretory proteins.

It has been pointed out that, in the case of heterologous proteins, in particular secretory proteins, which often have disulfide bonds, recombination of disulfide bonds by PDI as well as protein folding by peptidyl-prolyl-cis-trans isomerase (PPI) represent the rate-limiting step in the secretory process of proteins (Gething, M. J. and Sambrook, J. (1992) Nature 355: 33–45). It has also been demonstrated that PDI promotes folding of proteins consisting of a single domain such as RNase in vitro as well (Jaenicke, R. (1993) Curr. Opin. Struct. Biol. 3: 104–102).

On the other hand, because strain of methylotrophic yeasts grow using methanol as the sole carbon source and they have high yields of cells, they have been used for the production of materials for use in the synthetic chemical industry including, for example, aldehydes such as formaldehyde, epoxides, methylethylketone, and formic acid. Research has been conducted on the possible utilization of the cells per se as a protein source, and the utilization for production of cell components such as amino acids, vitamins, and the like, and some have been put into practical use. In recent years, furthermore, an expression system of heterologous genes using strain of methylotrophic yeasts as the host has been developed and it has been shown that said system has a higher productivity than Saccharomyces yeasts (Japanese Unexamined Patent Publication (Kokai) No. 5-344895).

Its productivity is high especially for secretory proteins. For example, the productivity of glucoamylase derived from filamentous fungi of the genus Rhizopus was 3.4 g/l, which is about 10 times higher than the productivity by Saccharomyces yeasts (Sakai, Y., et al. (1996) Biochim. Biophys. Acta 1308: 81–87). As the strain of methylotrophic yeast, there are known *Candida boidinii, Pichia pastoris, Hansenula polymorpha,* and the like.

When heterologous proteins are produced by secretory production using recombinant DNA technology, the efficiency of the secretion is thought to be increased by enhancing the speed of folding proteins. Based on such an idea, an example has been disclosed in which the amount secreted of human albumin was increased by about 60% on the average by coexpressing a human PDI gene with the desired gene in a Saccharomyces yeast (Japanese Unexamined Patent Publication (Kokai) No. 5-38771).

Formation or exchange of disulfide bonds which are necessary for appropriate folding of proteins requires environments suitable therefor. For that purpose, eukaryotic cells have intracellular compartments such as the ER or the Golgi apparatus, etc. While passing through the compartments, secretory proteins are subjected to suitable folding or addition of sugar chains and then are secreted out of the cell by means of exocytosis. Many of the secretory proteins of eukaryotic origin have intramolecular disulfide bonds, and formation and exchange of these disulfide bonds taking place in the ER are essential for formation of protein conformation and its secretion.

Accordingly, the PDI which catalyzes reactions for formation and/or exchange of disulfide bonds must be localized or stay in the ER. For this purpose the PDI has a unique amino acid sequence called an ER retention signal sequence at the C-terminal. As ER retention signal sequences there are known Lys-Asp-Glu-Leu (SEQ ID No. 2) for animals and His-Asp-Glu-Leu (SEQ ID No. 3) for Saccharomyces yeasts. When the human PDI gene as described above was expressed in a Saccharomyces yeast, the ER retention signal sequence of the human PDI did not fully function, which was possibly due to inadequate localization of the PDI in the ER. Thus, it is believed that even the highly expressed PDI gene did not cause enhancement in the PDI activity commensurate with the expression in the ER, and accordingly the increment of the amount secreted of the coexpressed secretory protein remained at a value of 60%.

In order for the PDI expressed in a strain of methylotrophic yeast to fully perform its functions, it is preferred to use the PDI derived from a strain of methylotrophic yeast. The reason why the strain of methylotrophic yeast has a high ability of secreting protein as described above is that recombination of disulfide bonds by the PDI which is the rate-limiting step of the protein secretion process takes place efficiently and that the PDI derived from the strain of methylotrophic yeast has a higher specific activity than the PDI derived from other sources or has a higher activity in the ER. However, the PDI of the strain of methylotrophic yeast or the gene thereof was unknown. Accordingly, no studies had been carried out on enhancement of productivity in the expression system of the strain of methylotrophic yeast by using the above PDI or the gene thereof.

SUMMARY OF THE INVENTION

The inventors have carried out intensive studies to clone the PDI gene carried by strain of methylotrophic yeast, to elucidate the nucleotide sequence thereof, and to reveal the characteristics of the PDI of strain of methylotrophic yeast. Thus, it is the object of the present invention to provide the PDI gene derived from strain of methylotrophic yeast in order to effect secretory production of heterologous genes by strain of methylotrophic yeast in a more efficient manner.

In order to attain the above-mentioned objective, the inventors have obtained a DNA fragment amplified by the PCR using as a primer an oligonucleotide synthesized based on an amino acid sequence of the conserved region present in the active site of the PDI. By means of the colony hybridization method using this amplified DNA fragment as a probe, the inventors have cloned the PDI gene of the strain of methylotrophic yeast *Candida boidinii,* and demonstrated the nucleotide sequence of said gene and the amino acid sequence of said PDI. Furthermore, by coexpressing the peroxidase gene derived from a filamentous fungus in the strain of methylotrophic yeast transformed with said PDI gene, the inventors have successfully increased by about 10 times the amount secreted of said peroxidase and have accomplished the present invention.

Thus, the present invention provides a protein derived from a strain of methylotrophic yeast which has a protein disulfide isomerase activity having the amino acid sequence as set forth in SEQ ID No. 1, or protein in which said amino acid sequence has been modified by deletion or addition of one or a few amino acids, or substitution with other amino acid(s) and which has a protein disulfide isomerase activity. The present invention also provides a gene encoding the PDI, a vector comprising said gene, and a host transformed with said vector, as well as a process for secreting in large amounts the desired protein by coexpressing the gene for said desired protein in said transformed yeast host.

BRIEF EXPLANATION OF THE DRAWINGS

FIGS. 3 (*a*) is a drawing that shows the construction of the expression vector pNPO3 of the ARP gene and (*b*) is a drawing that shows the construction of the expression vector PNRPD of the PDI1 gene.

FIG. 8 is a drawing that shows the ARP activity in the culture liquid of each of the cultured BPO17 strain, the BPP1 strain, and the BUL strain.

DETAILED DESCRIPTION

Figure 1:
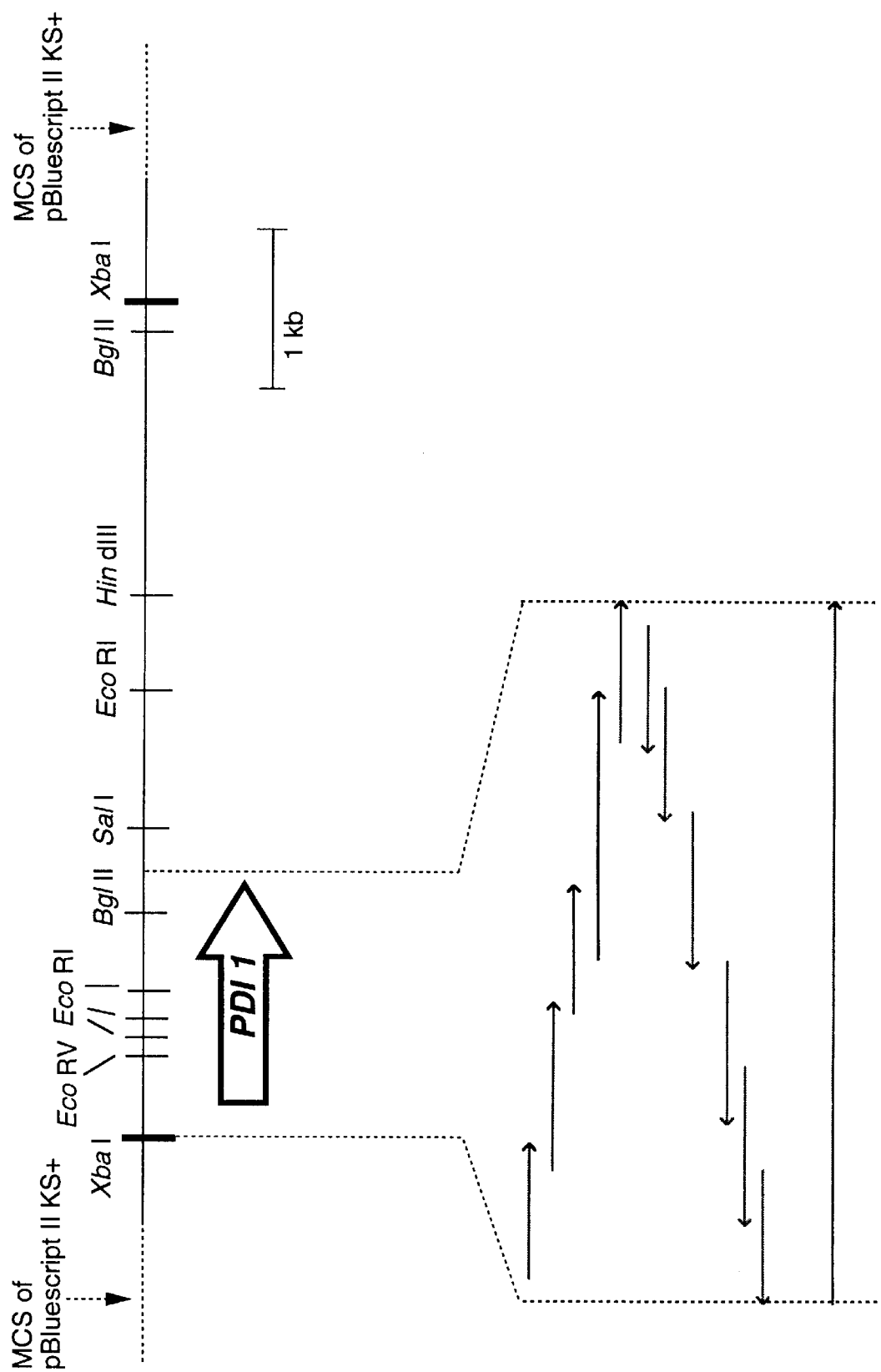
FIG. 1 is a drawing that shows a restriction enzyme map of the 6.2 kb DNA fragment containing the PDI1 gene of *Candida boidinii*, the region for which the nucleotide sequence was determined, and the position and direction of the PDI1 gene thereof.

The present invention is now explained in detail below.

First, the sequence, Cys-Gly-His-Cys, which is conserved in PDI's from a variety of sources as the active center of the exchange reaction of disulfide bonds was found at two sites in the amino acid sequence of the PDI derived from *Saccharomyces cereviceae*. Based on the amino acid sequence of PDI of *S. cereviceae* comprising said sequence, various primers for the PCR were designed with reference to the frequency of use of codons from the strain of methylotrophic yeast. Using these primers PCR reactions were carried out using the genomic DNA of the strain of methylotrophic yeast as a template, and the amino acid sequence deduced from the nucleotide sequence of the PCR reaction product thus obtained was confirmed to be analogous to the amino acid sequence of PDI of *S. cereviceae*.

The genomic DNA of a strain of methylotrophic yeast is completely digested with various restriction enzymes and is fractionated on agarose gel electrophoresis. Using the above-mentioned PCR products as a probe, Southern hybridization is carried out to find a restriction enzyme which gives the smallest DNA fragment containing the entire region of the PDI gene. Using the genomic DNA of the strain of methylotrophic yeast which has been completely digested with the restriction enzyme, a genomic library is created, which is then subjected to colony hybridization using the above-mentioned PCR product as a probe to select clones having the PDI gene.

Plasmid is extracted from the selected clone, and is subjected to Southern hybridization to confirm that the plasmid contains the sequence of the above-mentioned PCR product. Furthermore, a restriction map of the inserted fragments of this plasmid is created, based on which subcloning is conducted to obtain the smallest DNA fragment containing the PDI gene. The nucleotide sequence of the DNA fragment obtained is determined and the amino acid sequence of the PDI derived from the strain of methylotrophic yeast is analyzed.

The PDI gene thus obtained derived from the strain of methylotrophic yeast can be highly expressed in the strain of methylotrophic yeast to prepare the PDI. As an expression vector for the PDI gene known vectors may be used, and as an expression vector for the strain of methylotrophic yeast *Candida boidinii*, pNOTel or pTRex as described in Japanese Unexamined Patent Publication (Kokai) No. 5-344895 may be used. As the method for transforming the strain of methylotrophic yeast and the method for obtaining a transformant in which a foreign gene has been integrated into the chromosomal DNA thereof, a known method (Sakai, Y. et al. (1991), J. Bacteriol. 173: 7458–7463) can be used. Furthermore, the amount secreted of the desired secretory protein can be enhanced by coexpressing the PDI gene derived from the strain of methylotrophic yeast with the gene of the desired secretory protein in the strain of methylotrophic yeast.

Although the PDI derived from the strain of methylotrophic yeast had the ER retention signal Arg-Asp-Glu-Leu (SEQ ID No. 9) which is different from His-Asp-Glu-Leu (SEQ ID No. 3) derived from a Saccharomyces yeast, there is no doubt that the cells of *C. boidinii* recognize the former sequence which is of its own and the PDI is retained by the ER to fully perform its function. As expression vectors employed for expression of the PDI, those in which auxotrophic markers such as the above-mentioned pNOTel and pTRex have been replaced with the genes different from the ones used for the expression vector of the desired protein may be used. Furthermore, by imparting to the host strain of methylotrophic yeast auxotrophy corresponding to the two markers of the expression vector, transformation is possible by the method as described above. As the method for imparting auxotrophy to the strain of methylotrophic yeast, a known method (Sakai, Y. et al. (1991), J. Bacteriol. 173: 7458–7463) can be used.

EXAMPLES

The invention will be understood more readily with reference to the following examples; however these examples are intended to illustrate the invention and are not to be construed to limit the scope of the invention.

Example 1

From *Candida boidinii* strain S2 (Tani, Y., et al. (1985) Agric. Biol. Chem. 49: 2699–2706), the PDI gene was obtained and the nucleotide sequence thereof was determined. Incidentally, said strain has been designated *Candida boidinii* SAM1958 and deposited as an international deposition under the Budapest Treaty on Feb. 25, 1992, with National Institute of Bioscience and Human-Technology, Agency of Industrial Science and Technology, MITI, 1–3, Higashi 1-chome, Tsukuba-shi, Ibaraki, 305, Japan, with the accession number FERM BP-3766.

(1) Amplification by PCR

Two sequences were noted as the amino acid sequences in the PDI of *S. cereviceae* relating to Cys-Gly-His-Cys (SEQ ID No. 4), a sequence which is conserved in the PDI of various origins as the active center of the disulfide bond exchange reaction:

Pro-Trp-Cys-Gly-His-Cys-Lys (SEQ ID No. 5) (amino acids No. 59 through No. 65 in the amino acid sequence of the PDI of Saccharomyces yeast), Tyr-Ala-Pro-Trp-Cys-Gly-His (SEQ ID No. 6) (amino acids No. 402 through No. 408 in the amino acid sequence of the PDI of Saccharomyces yeast).

Referring to the frequency of use of *C. boidinii* codons, oligonucleotide having the following nucleotide sequence corresponding to the amino acid sequence was synthesized:

That is, as the sense primer, 5'-CCGGAATTC CCT(A) TGG TGT(C) GGT(A) CAT(C) TGT(C) AA-3' (SEQ ID No. 7), and as the antisense primer, 5'-CGCGGATCC TG A(T) CC A(G)CA CCA A(T)GG A(G/T)GC A(G)T-3' (SEQ ID No. 8) were synthesized. These oligonucleotides have on their 5'-end the sequence which recognizes EcoRI and BamHI, respectively. They are so designed that an EcoRI site is formed at the 5'-end and a BamHI site is formed at the 3'-end of the DNA fragments amplified by these two primers.

When PCR reaction was carried out using the genomic DNA of *C. boidinii* as a template and the above two oligonucleotides as a primer, an amplified DNA fragment of about 1 kb was observed. The amplified fragment was recovered and a DNA fragment of about 250 bp obtained by digestion of said fragment with a restriction enzyme EcoRI was inserted into the EcoRI-digested pBluescript II SK+. Analysis of the nucleotide sequence of the inserted fragment revealed a nucleotide sequence encoding an amino acid sequence having a high homology with the amino acid sequence of the PDI of *S. cereviceae,* and therefore this DNA fragment was concluded to be part of the PDI gene of *C. boidinii*.

(2) Southern hybridization analysis of the genomic DNA

Genomic DNA was isolated from the bacterial cells of *Candida boidinii* strain S2. As the method for isolating DNA, there is mentioned a method by Cryer (Cryer, D. R. et al. (1975) Meth. Cell. Biol. 12: 39–44). The genomic DNA of *Candida boidinii* strain S2 was cleaved with various restriction enzymes and then separated on a 0.7% agarose gel by electrophoresis. The separated DNA was transferred to and immobilized on a nylon membrane (manufactured by Amersham). A 250 bp DNA fragment containing the above-mentioned PDI gene was labelled with 32P using the Random Primer kit (manufactured by Amersham).

Figure 2:
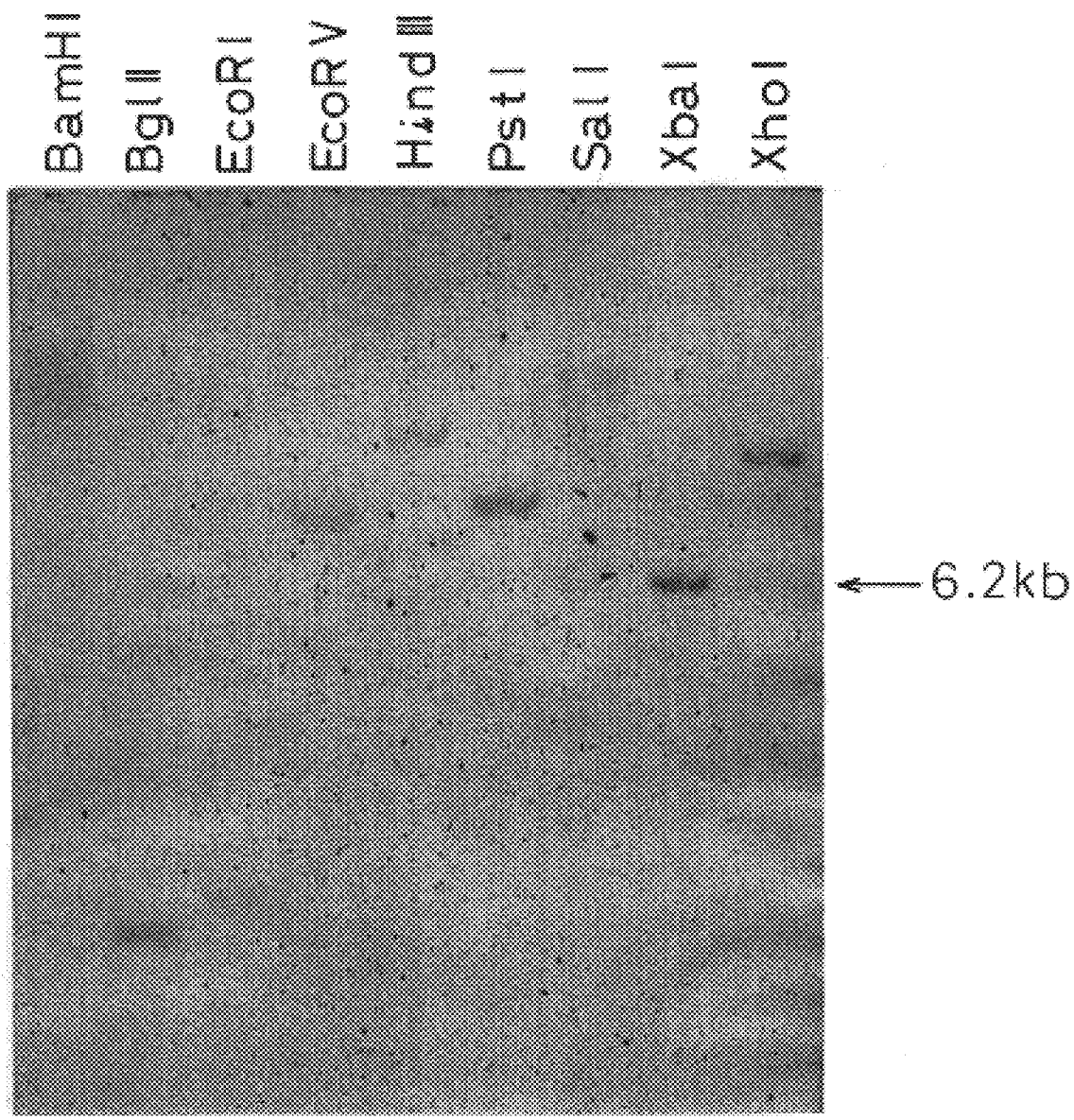
FIG. 2 is a drawing that shows the result of Southern hybridization demonstrating the presence of the PDI gene in *C. boidinii*.

The labelled DNA fragment was added to a 5×SSC–1% SDS–1×Denhardt solution to prepare a hybridization solution. This hybridization solution was added to the DNA-immobilized nylon membrane and encapsulated in a plastic bag. After the encapsulated plastic bag was incubated at 65° C. for 16 hours, the nylon membrane was removed from the plastic bag and washed in a 2×SSC–0.1% SDS solution at room temperature. Subsequently the nylon membrane was incubated in a 0.2×SSC–0.1% SDS solution and after the solution was replaced with a new one incubation at 65° C. for 30 minutes was repeated. After the membrane was washed in a 2×SSC, it was air-dried and subjected to autoradiography. As the smallest DNA fragment hybridizing to the above-mentioned 250 bp probe, an XbaI fragment of about 6.2 kb was found as shown in FIG. 2.

(3) Cloning of the PDI gene by colony hybridization

The genomic DNA of *Candida boidinii* strain S2 was completely digested with a restriction enzyme XbaI and fractionated on a 0.7% agarose gel electrophoresis. The agarose at around 6.2 kb was excised and the DNA fragment was recovered using a DNA cell (manufactured by Daiichi Kagaku). The recovered DNA was inserted into the XbaI-digested pBluescript II SK+, and *Escherichia coli* strain JM109 was transformed to prepare the genomic library of *Candida boidinii* strain S2.

The library was screened by colony hybridization using the above-mentioned 250 bp DNA fragment as a probe to obtain positive clones. The hybridization conditions were the same as that of the above-mentioned Southern hybridization. Plasmid was recovered from the positive clones to create a restriction enzyme map of the inserted DNA fragments. The restriction enzyme map so created is shown in FIG. 1. Subcloning was carried out based on the restriction enzyme map and the DNA fragment containing the PDI gene was limited to about 2 kb (the left hand side in FIG. 1) spanning from XbaI to SalI.

(4) Determination of the nucleotide sequence

The nucleotide sequence of the above DNA fragment of about 2 kb spanning from XbaI to SalI was determined. The DNA fragment was cloned into phage M13 in the both directions to prepare each of the double stranded DNA's (RF). These double stranded DNA's were allowed to react with *Escherichia coli* exonuclease III to prepare a double stranded DNA in which deletion has been introduced in one direction. A method for making an plasmid having a one-direction deletion insertion using exonuclease III has been described in detail on pages 289–305 in "Zoku Seikagaku Jikken Kouza (Sequel to the Series of Biochemistry Experiments), Vol. 1, Idenshi Kenkyuuhou (Methods for Studying Genes) II".

Each of the double stranded DNA's in which deletion has been inserted in one direction obtained in the above method was transformed into *E. coli* strain JM109 to make a phage clone in which deletion has been inserted in one direction. From each phage clone a double stranded DNA was prepared, for which the degree of deletion was investigated from the cleavage pattern by restriction enzymes, and then single stranded phage DNA's were prepared from appropriate clones. Using these single stranded phage DNA's as the template, the nucleotide sequence was determined by the dideoxy method (Sanger, F. et al. (1977) Proc. Natl. Acad. Sci. U.S.A. 74: 5463). By ligating the nucleotide sequence of each clone the nucleotide sequence of 2.0 kb spanning from the XbaI site to immediately before the SalI site in FIG. 2 was determined.

SEQ ID No. 1 shows the nucleotide sequence and the amino acid sequence of the PDI deduced from the nucleotide sequence. The PDI of *C. boidinii* was found to consist of 531 amino acids encoded by the nucleotide sequence from the base No. 367 through 1959 of the nucleotide sequence shown in SEQ ID No. 1, and was designated the PDI1 gene. The amino acid sequence of the PDI1 has shown a homology of 45% with the PDI derived from *S. cereviceae* and 22% with the human PDI. When analogous amino acids are considered, the homology was 64% with the PDI of *S. cereviceae* and 49% with the human PDI.

The sequence which has been conserved in the PDI of various origins as the active center of the disulfide bond exchange reaction of the PDI, i.e. Cys-Gly-His-Cys (SEQ ID No. 4), was found in two sites: the amino acid sequence from amino acids 61 to 64 and that from amino acids 408 to 411 of the amino acid sequence of SEQ ID No. 1. Furthermore, the ER retention signal sequence present in the C-terminal was Arg-Asp-Glu-Leu (SEQ ID No. 9), which was different from the PDI of *S. cereviceae*, His-Asp-Glu-Leu (SEQ ID No. 3), or Lys-Asp-Glu-Leu (SEQ ID No. 2) widely occurring in the PDI of mammals.

The measurement of the activity of protein disulfide isomerase can be performed by investigating the accelerating effect on reassembly of the scrambled ribonuclease A (RNase A) which was made by a method comprising reduction, denaturation and reoxidation. The degree of reassembly of ribonuclease A is quantitated using the degree of recovery of the enzymatic activity as an index (Japanese Unexamined Patent Publication (Kokai) No. 6-38771).

By measuring the PDI activity by the above-mentioned method, it was confirmed that the strain of methylotrophic yeast transformant containing the above DNA fragment had a higher protein disulfide isomerase activity than the untransformed strain of methylotrophic yeast as the control as shown in FIG. 1.

Example 2. Secretion of the desired heterologous protein

It was confirmed that the amount secreted of ARP is increased by coexpressing the PDI1 gene derived from the strain of methylotrophic yeast *C. boidinii* and the peroxidase gene (ARP) gene derived from a filamentous fungus *Arthromyces ramosus*. pNOTel used as an expression vector and the ARP expression vector pNOTelARP have been disclosed in Japanese Unexamined Patent Publication (Kokai) No. 5-344895. By exchanging the auxotrophic marker (URA3) of pNOTel for the LEU2 gene derived from *C. boidinii*, an expression vector having an auxotrophic marker different from pNOTel can be created. It is also possible to effect transformation by the two expression vectors mentioned above, by imparting to the strain of methylotrophic yeast auxotrophy corresponding to the markers of these two expression vectors. As a method for imparting auxotrophy to the strain of methylotrophic yeast, a known method (Sakai, Y. et al. (1991) J. Bacteriol. 173: 7458–7463) can be used.

(1) Construction of expression vectors

A 1.1 kb EcoRI DNA fragment containing the ARP gene was excised from plasmid pNOTelARP, and then inserted into the NotI site of pNOTel to create plasmid pNPO3 as shown in FIG. 3 (*a*).

Figure 4:
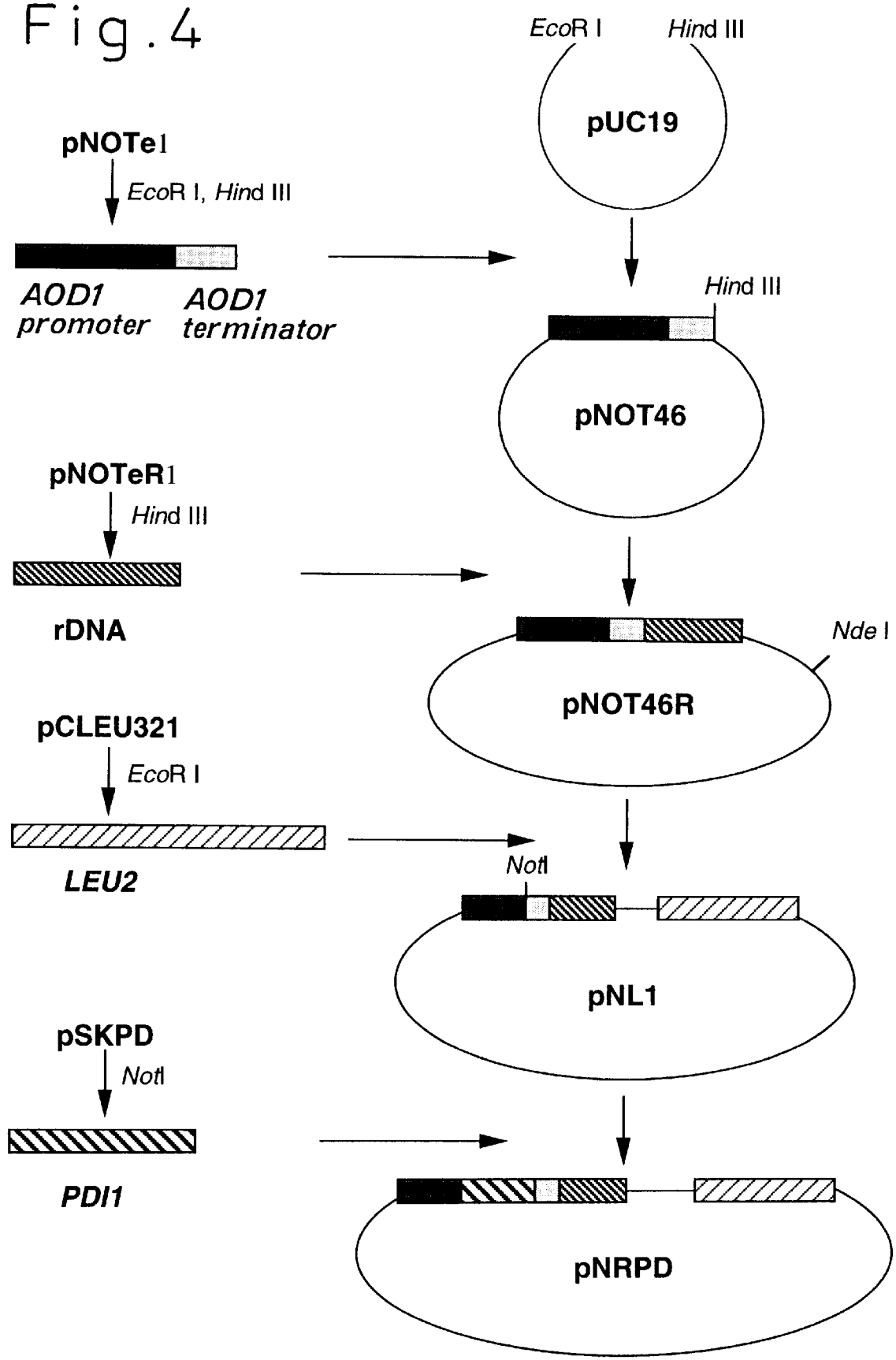
FIG. 4 is a drawing that shows a procedure of construction of the expression vector PNRPD for the PDI1 gene.

For the purpose of expressing the PDI1 gene, an expression vector having the LEU2 gene as an auxotrophic marker and the ribosome DNA (rDNA) of *C. boidinii* as a recombination site was created in the procedure as set forth in FIG. 4. To begin with, pNOTel was cleaved with EcoRI and HindIII and then a 2.0 kb DNA fragment containing the promoter and terminator of the alcohol oxidase gene (AOD1) of *C. boidinii* was excised and inserted into the EcoRI-HindIII site of pUC19 to create plasmid pNOT46. A DNA fragment containing rDNA derived from *C. boidinii* was obtained by the PCR method and was then inserted into the HindIII site of pNOT46 to create pNOT46R. Plasmid pCLEU321 (Sakai, Y. et al. (1992) J. Bacteriol. 174: 5988–5993) containing the LEU2 gene of *C. boidinii* was digested with EcoRI, and a DNA fragment containing a 3.2 kb LEU2 gene, which was rendered blunt-ended. After the blunt-ended 3.2 kb DNA fragment was digested with NdeI, it was inserted into the blunt-ended pNOT46R to create pNL1.

In order to integrate the above expression vectors, a NotI site was created on both ends of the PDI gene by the PCR method. As the sense primer, 5'-ATAAGAATGCGGCCG-CAAAATGAAGTTAACTAATTTCAAA-3' (SEQ ID No. 10), and as the antisense primer, 5'-ATAAGAATGCGG-CCGCTTATAATTCATCACGAACATCA-3' (SEQ ID No. 11) were synthesized. At the 5'-end of these two oligonucleotides there is a sequence recognized by NotI so that a NotI site may be created immediately before the initiation codon and immediately after the termination codon of the PDI1 gene in a DNA fragment amplified using these primers. Using the genomic DNA of *C. boidinii* as a template and the above two primers as a primer, PCR reaction was carried out, and the amplified 1.6 kb DNA fragment was digested with NotI, which was inserted into the NotI site of plasmid pBluescript II SK+ to create PSKPD. A 1.6 kb DNA fragment obtained by digesting pSKPD with NotI was inserted into the NotI site of the above pNL1 to create pNRPD as shown in FIG. 3 (*b*).

(2) Creation of a transformed yeast

Using the two expression vectors mentioned above in (1), a transformant of the strain of methylotrophic yeast *C. boidinii* was created. The bacterial strain used as the host is *C. boidinii* BUL (ura3, leu2) wherein the LEU2 gene of *C. boidinii* strain TK62 (ura3) (disclosed in Japanese Unexamined Patent Publication (Kokai) No. 5-344895) has been destructed. The LEU2 gene of *C. boidinii* has been disclosed by Sakai et al. (Sakai, Y. et al. (1992) J. Bacteriol. 174: 5988–5993). The method of transformation of *C. boidinii* has been disclosed in Japanese Unexamined Patent Publication (Kokai) No. 5-344895.

Figure 5A:
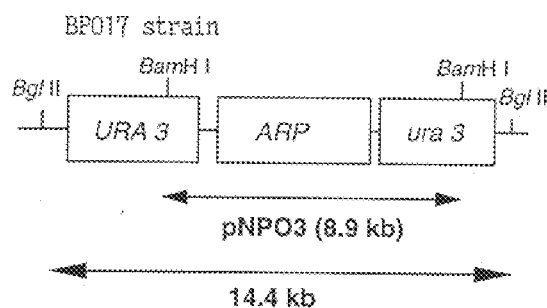
FIG. 5 is a schematic diagram showing the state in which the ARP gene has been integrated into the genomic DNA of the BPO17 strain, and a drawing that shows the result of Southern hybridization confirming it.
Figure 5B:
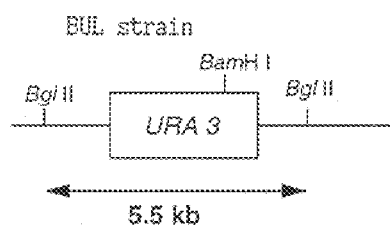
Figure 5C:
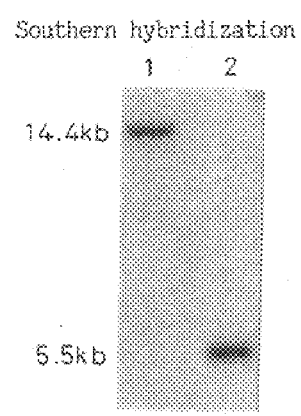

To begin with, a transformant of the ARP gene was created. After the ARP expression vector pNPO3 was linearized by digestion with BamHI, *C. boidinii* strain BUL (ura3, leu2) was transformed, and transformants were selected using Ura3+. As shown in FIGS. 5 A), B), in one of the transformants selected, the BPO17 strain, the entire region of pNPO3 containing the ARP gene has been integrated into the ura3 site by homologous recombination of the ura3 site on the chromosomal DNA of the host yeast BUL strain and the URA3 site in the expression vector pNPO3. This was confirmed by the fact, as shown in FIG. 5 C), that in Southern hybridization carried out using as a probe a 3.3 kb BamHI-SalI DNA fragment containing the entire region of the URA3 gene after the genomic DNA of the host BUL strain and the transformant BPO17 strain were digested with BglII, a 5.5 kb hybridizing band in the BUL strain and a 14.4 kb hybridizing band in the BPO17 strain were observed.

Figure 6A:
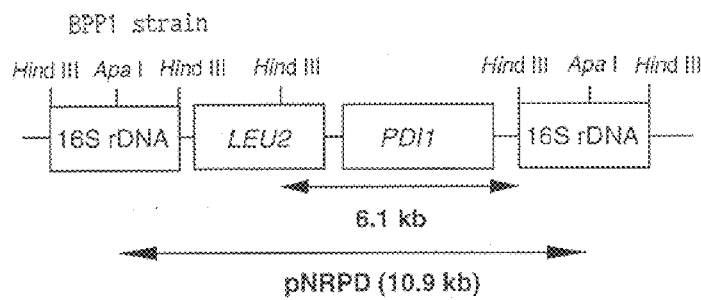
FIG. 6 is a schematic diagram showing the state in which the PDI1 gene has been integrated into the genomic DNA of the BPP1 strain, and a drawing that shows the result of Southern hybridization confirming it.
Figure 6B:
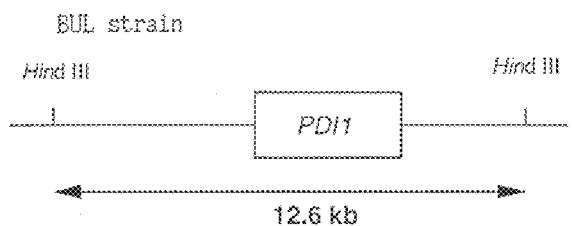
Figure 6C:
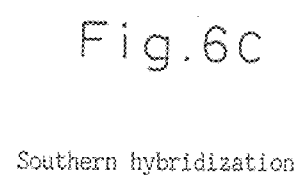

Next, using as the host *C. boidinii* strain BPO17 (leu2) which was transformed with the above-mentioned ARP gene, a transformant of the PDI1 gene was created. After the PDI1 expression vector PNRPD was linearized by digestion with ApaI, the BPO17 (leu2) strain was transformed and the BPP1 strain was obtained after selection with Leu+. In the BPP1 strain, as shown in FIGS. 6, A), B), the entire region of PNRPD containing the PDI1 gene has been integrated into the rDNA site by homologous recombination of the rDNA site on the chromosomal DNA of the host yeast BPO17 strain and the rDNA site in the expression vector pNPO3. Integration of the PDI1 gene into the chromosomal DNA was confirmed by the fact, as shown in FIG. 6 C), that in Southern hybridization carried out using as a probe a 1.6 kb DNA fragment containing the PDI1 gene obtained by digestion of pSKPD with NotI after the genomic DNA of the BUL strain, the host BPO17 strain and the transformant BPP1 strain were digested with HindIII, a band derived from the region containing a 12.6 kb intrinsic PDI1 gene from the BUL strain and the BPO17 strain and a 6.1 kb band derived from the expression vector pNRPD in addition to the above 12.6 kb band from the BPP1 strain were observed.

(3) Analysis of transformants mRNA was extracted from the BPO17 strain transformed with the ARP gene, the BPP1 strain transformed with the ARP gene and the PDI1 gene, and the BUL strain used as the host, and the amount expressed of the PDI1 gene was investigated by Northern hybridization. From the bacterial cells obtained from the above three strains cultured at 30° C. for 48 hours in the YM medium having methanol as the sole carbon source (Sakai, Y. et al. (1981) J. Gen. Microbiol. 123: 365–396), total RNA was extracted by ISOGEN (manufactured by Nihon Gene K. K.) and purified using BIOMAG mRNA purification kit (manufactured by PerSeptive Diagnostics). The purified mRNA was subjected to a 1.1% agarose gel electrophoresis (containing 20 mM MOPS buffer, 1 mM EDTA, 2.2 M formamide), and then blotted onto the nylon membrane. In the same condition as the Southern hybridization described in Example 1, hybridization was carried out. The probe used in the hybridization was 1.6 kb NotI DNA fragment derived from the above-mentioned pSKPD.

Figure 7:
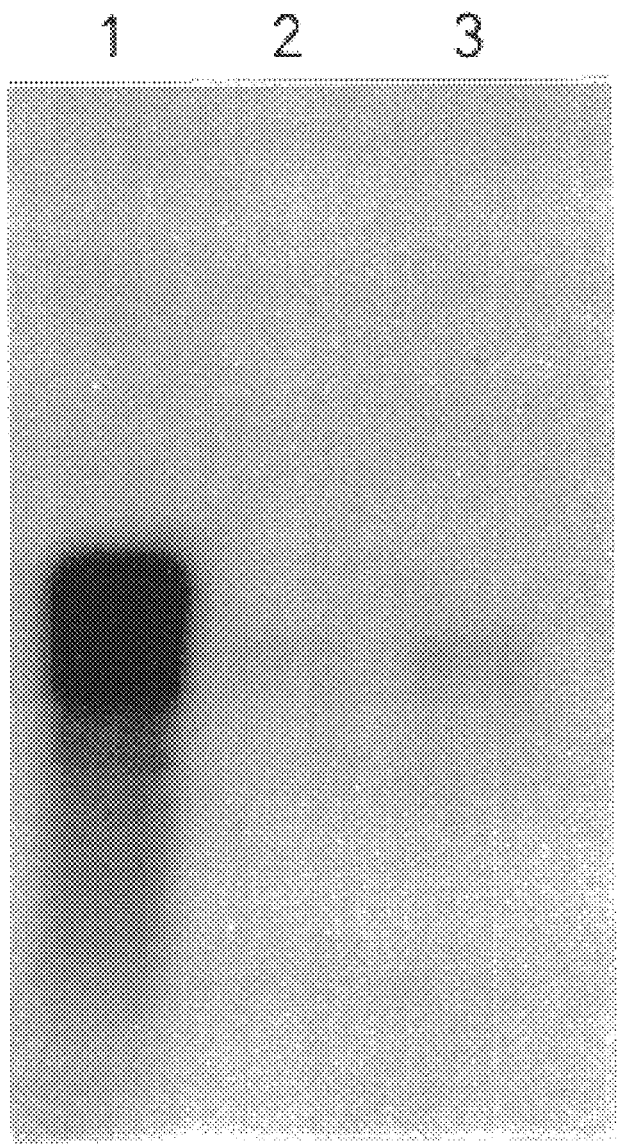
FIG. 7 is a drawing that shows the result of Northern analysis which analyzed the amount of the expressed PDI1 gene.

As shown in FIG. 7, strong expression of the PDI1 gene was observed in the BPP1 strain which was transformed with the PDI1 gene and weak expression of possibly the intrinsic PDI1 gene was observed in the BUL strain and the BPO17 strain.

The above three bacterial strains were cultured in the YM medium containing methanol as the sole carbon source at 30° C. for 48 hours, and then the PDI activity in the bacterial cells was measured. The harvested cells were suspended in 50 mM potassium phosphate buffer, pH 7.5, and transferred into a 2 ml Eppendorf tube, to which was added an equal volume of zirconium beads (0.5 mm in diameter). A procedure of vigorous stirring of the tube for 30 seconds using the Beads Beader (Model 3110BX, Biospec Products) followed by cooling on ice for 30 seconds was repeated for six times. The disrupted cells were centrifuged at 4° C. at 16,000×g for 5 minutes and then the enzymatic activity of the supernatant was measured.

The measurement of the PDI activity was carried out in accordance with the method of Hillson et al. (Hisllson, D. A. et al. (1984) Methods Enzymol. 107: 281–294). Thus, one ml of the final reaction mixture contains 50 mM potassium phosphate buffer, pH 7.5, 500 μg of scrambled RNase, and 0.01 mM of dithiothreitol. After the reaction mixture was incubated for 10 minutes, 10 μl was sampled out, to which 3 ml of the TKM buffer (50 mM Tris-HCl, pH 7.5, 25 mM KC1, 5 mM MgCl) containing 0.25 mg yeast RNA was added and then RNase activity was determined by measuring absorbance at 260 nm in a UV cuvette at 30° C. for 2 minutes. One unit of the enzymatic activity was defined as the amount of enzyme which increases the absorbance at 260 nm per one minute.

As shown in Table 1, the PDI activity in the bacterial cells was higher in the BPP1 strain transformed with the PDI gene than the BPO17 strain transformed with the ARP gene alone or the BUL strain used as the host by a factor of 9 or more.

TABLE 1

| | Strain | | |
|---|---|---|---|
| Enzyme | BUL | BPO17 | BPP1 |
| PDI | <0.1* | <0.1* | 0.896 |

*The levels of BUL and BPO17 were below the detection limit.

(4) Secretory expression of the ARP

The BPO17 strain transformed with the ARP gene, the BPP1 strain transformed with both of the ARP gene and the PDI1 gene, and the BUL strain used as the host were cultivated in the YM medium containing methanol as the sole carbon source, and the ARP activity in the culture liquid was compared. As shown in FIG. 8, the ARP activity in the culture liquid of the BPP1 strain coexpressed with the ARP gene and the PDI1 gene reached a maximum of 0.024 U/ml at 84 hours after cultivation. In the BPO17 strain in which the ARP gene only was expressed, the ARP activity in the culture liquid reached a maximum of 0.002 U/ml at 84 hours after cultivation, while no ARP activity was observed in the culture liquid of the BUL strain used as the host. The result revealed that by coexpressing the PDI1 gene and the ARP gene the amount secreted of ARP increased by about 10 fold.

The present invention made it possible to obtain the PDI gene of the strain of methylotrophic yeast and to obtain the PDI enzyme by expressing said gene in large quantities using said strain of methylotrophic yeast. Furthermore, by coexpressing said gene with the gene of the desired secretory protein in the strain of methylotrophic yeast it became possible to drastically increase the amount produced of the desired protein.

What is claimed is:

1. An isolated gene encoding a protein having the amino acid sequence as set forth in SEQ ID No: 12.

2. The isolated gene of claim 1, wherein the gene has the nucleotide sequence of the coding region as set forth in SEQ ID No: 1.

3. An isolated gene according to claim 1 having a nucleotide sequence as set forth in Seq. ID No. 1.

4. A vector comprising an isolated gene according to claim 1.

5. A transformant obtained by transforming a host with a vector according to claim 4.

6. A transformant according to claim 5 wherein the host is a strain of methylotrophic yeast.

7. A transformant according to claim 6 wherein the strain of methylotrophic yeast is *Candida boidinii*.

8. A method of producing a protein having a protein disulfide isomerase activity, which method comprises culturing a transformant according to claim 5, and then recovering the protein from the culture.

9. A method for producing a peptide or a protein encoded by a heterologous structural gene, which method comprises culturing a transformant cotransformed with a vector according to claim 4 and a vector having a heterologous structural gene and then recovering an expression product of the heterologous structural gene, which is the peptide or the protein, from the culture.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 2030 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Candida boidinii
    (B) STRAIN: S2

(ix) FEATURE:
    (A) NAME/KEY: CDS
    (B) LOCATION: 367..1960

(xi) SEQUENCE DESCRIPTION: SEQ ID NO:1:

```
AGAGCGCTCT CCACTCACTC ATTATTCATC CAGTATCTCC TCCAAGGTTG TGAACAATTT      60

CACTCACTTG CCTTGCTTTA CCATCTACTC AATCGTTTCA TTTACTCCTG TATCATTCCA     120

CCATTTCATC ACTTTTTCAT ATCTAGTAAC TAAATGTCTA AGCAACGATA ATCTTTCAGC     180

AGATTCGCTC TTCTTTGATT CAATTGATCC TTTCATAGAC AGATCACTGA CACGTAAATA     240

CTTACATAGA TATATATATA TATATATGTA AATTTACTTT CGTCATTACT CAATTGATTC     300

CATTTAATAC ATTCATAGTA TAATATATTG ACTTAAATAT ATTTACATAT ACACATAACA     360

TTTAAA ATG AAG TTA ACT AAT TTC AAA GTT ATT GCC ACA ATT CTT GCT        408
       Met Lys Leu Thr Asn Phe Lys Val Ile Ala Thr Ile Leu Ala
        1               5                  10

TGT TTA ACA GTT GTT AGA GCT GAT GAT GGT GGT GCC ATT GCA TCT CCA       456
Cys Leu Thr Val Val Arg Ala Asp Asp Gly Gly Ala Ile Ala Ser Pro
 15                  20                  25                  30

GAT TCC GCT GTT GTT AAA TTA ACT GCT GAT TCA TTC GAA TCA TTC ATG       504
Asp Ser Ala Val Val Lys Leu Thr Ala Asp Ser Phe Glu Ser Phe Met
                 35                  40                  45

AAA GAA AAT CCA TTA GTC TTA GCT GAA TTT TTT GCT CCT TGG TGT GGT       552
Lys Glu Asn Pro Leu Val Leu Ala Glu Phe Phe Ala Pro Trp Cys Gly
                     50                  55                  60

CAT TGT AAA AGA TTG GGT CCT GAA TTT CAA GTT GCT GCT GAT AAA TTA       600
His Cys Lys Arg Leu Gly Pro Glu Phe Gln Val Ala Ala Asp Lys Leu
                 65                  70                  75

GTT GAA AAA GAT ATT AGA TTA GCT CAA ATT GAT TGT ACC GAA GAA AAA       648
Val Glu Lys Asp Ile Arg Leu Ala Gln Ile Asp Cys Thr Glu Glu Lys
             80                  85                  90

GAT TTA TGT TCT TCT TAT GGT ATT AAA GGT TAC CCA ACT TTA AAA GTC       696
Asp Leu Cys Ser Ser Tyr Gly Ile Lys Gly Tyr Pro Thr Leu Lys Val
 95                 100                 105                 110

TTT AGA GGT TAC GAA AAT GAA CCT TCT GAT TAT GCT GGT CAA AGA ACT       744
Phe Arg Gly Tyr Glu Asn Glu Pro Ser Asp Tyr Ala Gly Gln Arg Thr
                    115                 120                 125

TCA GAT TCA ATC ATT TCT TAT ATG GTT AAA CAA TCA ACC CCA CCT GTC       792
Ser Asp Ser Ile Ile Ser Tyr Met Val Lys Gln Ser Thr Pro Pro Val
                130                 135                 140

TCC ATC GTT GAT GAT CTC TCA GAT ATC GAA GAT ACA ATT AAA GAA TCA       840
Ser Ile Val Asp Asp Leu Ser Asp Ile Glu Asp Thr Ile Lys Glu Ser
            145                 150                 155

AAT GAT CCT GTC TTT ATT CAA GTC TTA CCA AAA GGT TCT AAA TCT GTT       888
Asn Asp Pro Val Phe Ile Gln Val Leu Pro Lys Gly Ser Lys Ser Val
        160                 165                 170

GAA GCC GGT AAC TCA ACT TTC TTT GAA ATC GCT AAT GGT TTA AGA GAT       936
Glu Ala Gly Asn Ser Thr Phe Phe Glu Ile Ala Asn Gly Leu Arg Asp
175                 180                 185                 190

AAC TAC TCT TTT ATT TCA ACA ACA AGT ACT GAA TTC TCT TCA AAA TAC       984
Asn Tyr Ser Phe Ile Ser Thr Thr Ser Thr Glu Phe Ser Ser Lys Tyr
                    195                 200                 205
```

-continued

| | | |
|---|---|---|
| TTG AAA GGT ATT AAA AAA TCA GAT ACT CCA TCT TAT ATT CTC TTT AGA<br>Leu Lys Gly Ile Lys Lys Ser Asp Thr Pro Ser Tyr Ile Leu Phe Arg<br>210 215 220 | | 1032 |
| CCA AAT GAA GAA TTG TCT GAT GCT TCA ATC TAT AAA TTT GAT GAA ATT<br>Pro Asn Glu Glu Leu Ser Asp Ala Ser Ile Tyr Lys Phe Asp Glu Ile<br>225 230 235 | | 1080 |
| GAT GAT ACT CAT TTA ATC GAA TTC TTA AAC GTT GAA TCA AAA CCT TTA<br>Asp Asp Thr His Leu Ile Glu Phe Leu Asn Val Glu Ser Lys Pro Leu<br>240 245 250 | | 1128 |
| TTC GGT GAA ATG GAT GGT TCT TCT TTC CAA TCT TAT ATG GAA ATG AAA<br>Phe Gly Glu Met Asp Gly Ser Ser Phe Gln Ser Tyr Met Glu Met Lys<br>255 260 265 270 | | 1176 |
| TTA CCA GTT GCT TAT TAT TTC TAT AAT GAA ATC TCT GAA AAA GAT GCC<br>Leu Pro Val Ala Tyr Tyr Phe Tyr Asn Glu Ile Ser Glu Lys Asp Ala<br>275 280 285 | | 1224 |
| GTC TCT GAT GCC ATC AGT AAA TTA GCT AAA ACT CAT AGA GGT AAA GTT<br>Val Ser Asp Ala Ile Ser Lys Leu Ala Lys Thr His Arg Gly Lys Val<br>290 295 300 | | 1272 |
| AAT TTC GTT GGT TTA GAC GCT TCT AAA TAT GGT TTA CAC GCT AAG AAT<br>Asn Phe Val Gly Leu Asp Ala Ser Lys Tyr Gly Leu His Ala Lys Asn<br>305 310 315 | | 1320 |
| ATT AAC ATG AAG GAA GAA TTC CCT CTT TTC GCT ATT CAC GAT TTA GCA<br>Ile Asn Met Lys Glu Glu Phe Pro Leu Phe Ala Ile His Asp Leu Ala<br>320 325 330 | | 1368 |
| ACT GAA TTA AAA TAC GGT ATC TCC CAA GAT AAA CCA TTA GAT AAT AAA<br>Thr Glu Leu Lys Tyr Gly Ile Ser Gln Asp Lys Pro Leu Asp Asn Lys<br>335 340 345 350 | | 1416 |
| TTA ATT CCA AAA TTC GTT GAA GAT TTC GTT GCT GGT AAA TTA GAA GCA<br>Leu Ile Pro Lys Phe Val Glu Asp Phe Val Ala Gly Lys Leu Glu Ala<br>355 360 365 | | 1464 |
| ATC ATT AAA TCA GAA CCA ATC CCA GAA ACT CAA GAT TCT CCA GTT TAC<br>Ile Ile Lys Ser Glu Pro Ile Pro Glu Thr Gln Asp Ser Pro Val Tyr<br>370 375 380 | | 1512 |
| CAT TTA GTC GGT AAA GAA CAT GAT AAA ATT ATT ACC TCT GAT AAA GAT<br>His Leu Val Gly Lys Glu His Asp Lys Ile Ile Thr Ser Asp Lys Asp<br>385 390 395 | | 1560 |
| GTC TTA GTT AAA TAT TAC GCT CCA TGG TGT GGT CAC TGT AAA AAA TTA<br>Val Leu Val Lys Tyr Tyr Ala Pro Trp Cys Gly His Cys Lys Lys Leu<br>400 405 410 | | 1608 |
| GCT CCA GTC TTT GAA GAA TTA GCT GCT GTT TAT GAA TCA GTT GCT CCA<br>Ala Pro Val Phe Glu Glu Leu Ala Ala Val Tyr Glu Ser Val Ala Pro<br>415 420 425 430 | | 1656 |
| GGT AAA GTC TTA TTA GCT GAT TTA GAT CAT ACT GAA AAT GAT GTC ACC<br>Gly Lys Val Leu Leu Ala Asp Leu Asp His Thr Glu Asn Asp Val Thr<br>435 440 445 | | 1704 |
| GGT GTT CAC ATT GAA GGT TAC CCA ACT ATC GTC TTA TAC CCA GCC GAT<br>Gly Val His Ile Glu Gly Tyr Pro Thr Ile Val Leu Tyr Pro Ala Asp<br>450 455 460 | | 1752 |
| GGT TCA GAA CCA GTT GTT TAC GAA GGT AAC AGA TCT TTT GAA TCT TTC<br>Gly Ser Glu Pro Val Val Tyr Glu Gly Asn Arg Ser Phe Glu Ser Phe<br>465 470 475 | | 1800 |
| TCC GAT TTC ATT AAA GAA AAA GGT TCA TCA GGT GTT GAT GCT AAT GCA<br>Ser Asp Phe Ile Lys Glu Lys Gly Ser Ser Gly Val Asp Ala Asn Ala<br>480 485 490 | | 1848 |
| TTA AAA GAA CCT TAC CCA GAA GAA GGT ACT GAA GGT GCT CCA GTT GAT<br>Leu Lys Glu Pro Tyr Pro Glu Glu Gly Thr Glu Gly Ala Pro Val Asp<br>495 500 505 510 | | 1896 |
| CCA GAA TCA GTT GGT GAT GCT GAA AAA GAA GAT GAT TCT GCT GCT GAT<br>Pro Glu Ser Val Gly Asp Ala Glu Lys Glu Asp Asp Ser Ala Ala Asp<br>515 520 525 | | 1944 |

```
GTT CGT GAT GAA TTA T AAACAAGTAG AATTAATTAT AAATTGATTA            1990
Val Arg Asp Glu Leu
            530

AATAGTCTTC TAAAAATTAA ATTTAAAATA ATAAAAAAAA                        2030

(2) INFORMATION FOR SEQ ID NO:2:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:2:

Lys Asp Glu Leu
1

(2) INFORMATION FOR SEQ ID NO:3:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:3:

His Asp Glu Leu
1

(2) INFORMATION FOR SEQ ID NO:4:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:4:

Cys Gly His Cys
1

(2) INFORMATION FOR SEQ ID NO:5:

(i) SEQUENCE CHARACTERISTICS:
           (A) LENGTH: 7 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:5:

Pro Trp Cys Gly His Cys Lys
1               5

(2) INFORMATION FOR SEQ ID NO:6:

(i) SEQUENCE CHARACTERISTICS:
           (A) LENGTH: 7 amino acids
           (B) TYPE: amino acid
           (C) STRANDEDNESS:
           (D) TOPOLOGY: linear
```

(ii) MOLECULE TYPE: peptide (xi) SEQUENCE DESCRIPTION: SEQ ID NO:6:

Tyr Ala Pro Trp Cys Gly His
1               5

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCGGAATTCC CWTGGTGTYG GWCAYTGYAA                                    30

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CGCGGATCCT CWCCRCACCA WGGDGCRT                                      28

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Arg Asp Glu Leu
1

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "chemical synthetic DNA"

(xi) SEQUENCE DESCRIPTION: SEQ ID NO:10:

ATAAGAATGC GGCCGCAAAA TGAAGTTAAC TAATTTCAAA                         40

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "chemical synthetic DNA"

(xi) SEQUENCE DESCRIPTION: SEQ ID NO:11:

ATAAGAATGC GGCCGCTTAT AATTCATCAC GAACATCA                     38

(2) INFORMATION FOR SEQ ID NO:12:

(i) SEQUENCE CHARACTERISTICS:
        (A) LENGTH: 531 amino acids
        (B) TYPE: amino acid
        (D) TOPOLOGY: linear (ii) MOLECULE TYPE: protein (xi) SEQUENCE DESCRIPTION: SEQ ID NO:12:

```
Met Lys Leu Thr Asn Phe Lys Val Ile Ala Thr Ile Leu Ala Cys Leu
 1               5                  10                  15

Thr Val Val Arg Ala Asp Asp Gly Gly Ala Ile Ala Ser Pro Asp Ser
             20                  25                  30

Ala Val Val Lys Leu Thr Ala Asp Ser Phe Glu Ser Phe Met Lys Glu
         35                  40                  45

Asn Pro Leu Val Leu Ala Glu Phe Phe Ala Pro Trp Cys Gly His Cys
     50                  55                  60

Lys Arg Leu Gly Pro Glu Phe Gln Val Ala Ala Asp Lys Leu Val Glu
 65                  70                  75                  80

Lys Asp Ile Arg Leu Ala Gln Ile Asp Cys Thr Glu Lys Asp Leu
                 85                  90                  95

Cys Ser Ser Tyr Gly Ile Lys Gly Tyr Pro Thr Leu Lys Val Phe Arg
                100                 105                 110

Gly Tyr Glu Asn Glu Pro Ser Asp Tyr Ala Gly Gln Arg Thr Ser Asp
            115                 120                 125

Ser Ile Ile Ser Tyr Met Val Lys Gln Ser Thr Pro Pro Val Ser Ile
        130                 135                 140

Val Asp Asp Leu Ser Asp Ile Glu Asp Thr Ile Lys Glu Ser Asn Asp
145                 150                 155                 160

Pro Val Phe Ile Gln Val Leu Pro Lys Gly Ser Lys Ser Val Glu Ala
                165                 170                 175

Gly Asn Ser Thr Phe Phe Glu Ile Ala Asn Gly Leu Arg Asp Asn Tyr
            180                 185                 190

Ser Phe Ile Ser Thr Thr Ser Thr Glu Phe Ser Ser Lys Tyr Leu Lys
        195                 200                 205

Gly Ile Lys Lys Ser Asp Thr Pro Ser Tyr Ile Leu Phe Arg Pro Asn
    210                 215                 220

Glu Glu Leu Ser Asp Ala Ser Ile Tyr Lys Phe Asp Glu Ile Asp Asp
225                 230                 235                 240

Thr His Leu Ile Glu Phe Leu Asn Val Glu Ser Lys Pro Leu Phe Gly
                245                 250                 255

Glu Met Asp Gly Ser Ser Phe Gln Ser Tyr Met Glu Met Lys Leu Pro
            260                 265                 270

Val Ala Tyr Tyr Phe Tyr Asn Glu Ile Ser Glu Lys Asp Ala Val Ser
        275                 280                 285

Asp Ala Ile Ser Lys Leu Ala Lys Thr His Arg Gly Lys Val Asn Phe
    290                 295                 300

Val Gly Leu Asp Ala Ser Lys Tyr Gly Leu His Ala Lys Asn Ile Asn
305                 310                 315                 320

Met Lys Glu Glu Phe Pro Leu Phe Ala Ile His Asp Leu Ala Thr Glu
                325                 330                 335
```

-continued

```
Leu Lys Tyr Gly Ile Ser Gln Asp Lys Pro Leu Asp Asn Lys Leu Ile
            340             345             350

Pro Lys Phe Val Glu Asp Phe Val Ala Gly Lys Leu Glu Ala Ile Ile
            355             360             365

Lys Ser Glu Pro Ile Pro Glu Thr Gln Asp Ser Pro Val Tyr His Leu
            370             375             380

Val Gly Lys Glu His Asp Lys Ile Ile Thr Ser Asp Lys Asp Val Leu
385             390             395             400

Val Lys Tyr Tyr Ala Pro Trp Cys Gly His Cys Lys Lys Leu Ala Pro
            405             410             415

Val Phe Glu Glu Leu Ala Ala Val Tyr Glu Ser Val Ala Pro Gly Lys
            420             425             430

Val Leu Leu Ala Asp Leu Asp His Thr Glu Asn Asp Val Thr Gly Val
            435             440             445

His Ile Glu Gly Tyr Pro Thr Ile Val Leu Tyr Pro Ala Asp Gly Ser
    450             455             460

Glu Pro Val Val Tyr Glu Gly Asn Arg Ser Phe Glu Ser Phe Ser Asp
465             470             475             480

Phe Ile Lys Glu Lys Gly Ser Ser Gly Val Asp Ala Asn Ala Leu Lys
            485             490             495

Glu Pro Tyr Pro Glu Glu Gly Thr Glu Gly Ala Pro Val Asp Pro Glu
            500             505             510

Ser Val Gly Asp Ala Glu Lys Glu Asp Asp Ser Ala Ala Asp Val Arg
            515             520             525

Asp Glu Leu
    530
```